(12) United States Patent
Tanimoto et al.

(10) Patent No.: US 6,638,890 B2
(45) Date of Patent: Oct. 28, 2003

(54) MODIFIED CARRIER, COMPLEX OXIDE CATALYST AND PROCESS FOR PREPARATION OF ACRYLIC ACID

(75) Inventors: Michio Tanimoto, Himeji (JP); Hiromi Yunoki, Himeji (JP); Daisuke Nakamura, Himeji (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 10/284,195

(22) Filed: Oct. 31, 2002

(65) Prior Publication Data

US 2003/0065216 A1 Apr. 3, 2003

Related U.S. Application Data

(62) Division of application No. 09/729,428, filed on Dec. 5, 2000, now abandoned.

(30) Foreign Application Priority Data

Dec. 8, 1999  (JP) ............................................ 11-349069

(51) Int. Cl.[7] .......................... B01J 23/28; B01J 23/22; B01J 23/72; B01J 27/18; B01J 21/06
(52) U.S. Cl. ...................... 502/300; 502/202; 502/204; 502/205; 502/206; 502/208; 502/209; 502/210; 502/211; 502/212; 502/232; 502/240; 502/244; 502/246; 502/247; 502/248; 502/249; 502/254; 502/255; 502/258; 502/259; 502/260; 502/263; 502/302; 502/303; 502/304; 502/305; 502/306; 502/307; 502/308; 502/309; 502/310; 502/311; 502/312; 502/317; 502/318
(58) Field of Search ................................ 502/202, 204, 502/205, 206, 208, 209, 210, 211, 212, 232, 240, 242, 243, 244, 246, 247, 248, 249, 254, 255, 258, 259, 260, 263, 300, 302, 303, 304, 305, 306, 307, 308, 309, 310, 311, 312, 317, 318, 182, 183, 184, 185, 200

(56) References Cited

U.S. PATENT DOCUMENTS 4,051,180 A * 9/1977 Shaw et al.
RE29,901 E * 2/1979 Wada et al.

FOREIGN PATENT DOCUMENTS

EP  0227461  * 7/1987
EP  0711745  * 5/1996
EP  0792866  * 9/1997

* cited by examiner

Primary Examiner—Elizabeth D. Wood
(74) Attorney, Agent, or Firm—Sherman & Shalloway

(57) ABSTRACT

A modified carrier carrying on at least a part of an inert carrier surface an oxide which is represented by the formula (1): $X_a Y_b Z_c O_d$ (wherein X is at least an element selected from alkaline earth metals; Y is at least an element selected from Si, Al, Ti and Zr; Z is at least an element selected from Group IA elements and Group IIIb elements of the periodic table, B, Fe, Bi, Co, Ni and Mn; and O is oxygen; a, b, c and d denote the atomic ratios of X, Y, Z and O, respectively, where $a=1$, $0<b \leq 100$, $0 \leq c \leq 10$, and d is a numerical value determined by the extents of oxidation of the other elements) is provided. A catalyst formed with the use of this modified carrier carrying a complex oxide containing Mo and V is useful as a vapor phase catalytic oxidation catalyst, and is particularly suitable as a catalyst for preparing acrylic acid through vapor phase catalytic oxidation of acrolein.

2 Claims, No Drawings

MODIFIED CARRIER, COMPLEX OXIDE CATALYST AND PROCESS FOR PREPARATION OF ACRYLIC ACID

CROSS REFERENCE TO RELATED APPLICATION

This application is a divisional of application Ser. No. 09/729,428, filed on Dec. 5, 2000, now abandoned which claims priority from Japanese Patent Application 349069/99 filed Dec. 8, 1999.

1. Field of Industrial Utilization

This invention relates to catalyst carrier, complex oxide catalyst and production process of acrylic acid. More particularly, the invention relates to a modified carrier suitable as a carrier of a catalyst for making acrylic acid from acrolein by vapor phase catalytic oxidation reaction, a catalyst formed by supporting a complex oxide catalyst on said modified carrier, and to a producing process of acrylic acid using said catalyst.

2. Prior Art

A large number of improved catalysts for preparing acrylic acid through vapor phase catalytic oxidation reaction of acrolein have been proposed. For example, Japanese Patent Publication No. 12129/69 described a catalyst formed of molybdenum, vanadium and tungsten; Publication No. 11371/74, that formed of molybdenum, vanadium, copper, tungsten and chromium; Publication No. 25914/75, that formed of molybdenum and vanadium; and Laid-open (Kokai) Patent Application, Kokai No. 85091/77, that formed of molybdenum, vanadium, copper and at least one element of antimony and germanium.

However, these conventional catalysts are not fully satisfactory for industrial working, because of such defects that the yield of the object product, i.e., acrylic acid, is insufficient and deterioration rate in activity is high, leading to short catalyst life. Therefore, development of catalysts which excel in stability and enable acrylic acid production at high yield over prolonged periods has been in demand.

[Problem to Be Solved by the Invention]

Accordingly, one of the objects of the present invention is to provide a carrier, in particular, a novel carrier suitable for use in production of acrylic acid through vapor phase catalytic oxidation of acrolein.

Another object of the invention is to provide a complex oxide catalyst, in particular, a complex oxide catalyst which is suitable for producing acrylic acid through vapor phase catalytic oxidation of acrolein.

A further object of the present invention is to provide a process for preparing acrylic acid at high yield over prolonged periods, by oxidizing acrolein in the presence of catalyst at vapor phase with molecular oxygen or a molecular oxygen-containing gas.

[Means to Solve the Problem]

We have discovered that a product obtained by having a commonly used inert carrier carry an oxide containing at least an element selected from alkaline earth metals, at least an element selected from silicon, aluminum, zirconium and titanium, and optionally at least an element selected from Group IA elements and Group IIIb elements of the periodic table, boron, iron, bismuth, cobalt, nickel and manganese on at least a part of its surface (which product is hereafter referred to as a modified carrier) is useful as a carrier of the oxidation catalyst; and that the use of, for example, a product which is obtained by having the modified carrier carry a complex oxide containing molybdenum and vanadium (which product is hereafter referred to as a complex oxide catalyst) as the catalyst in the oxidation reaction of acrolein enables production of acrylic acid in high yield stably over prolonged periods.

Thus, according to the invention, a modified carrier is provided, which is characterized in that an inert carrier is caused to carry, on at least a part of its surface, an oxide expressed by the formula (1):

$$X_a Y_b Z_c O_d \qquad (1)$$

(where X is at least an element selected from alkaline earth metals, Y is at least an element selected from silicon, aluminum, titanium and zirconium, Z is at least an element selected from Group IA elements and Group IIIb elements of the periodic table, boron, iron, bismuth, cobalt, nickel and manganese, and O is oxygen; a, b, c and d denote the atomic ratios of X, Y, Z and O, respectively; and where a=1, 0<b≦100 (preferably 0.01≦b≦100), 0≦c≦10, and d is a numerical value determined by the extents of oxidation of the other elements).

According to the invention, also a complex oxide catalyst characterized by having a complex oxide containing molybdenum and vanadium, in particular, a complex oxide which is expressed by the following general formula (2):

$$Mo_e V_f W_g Cu_h A_i B_j O_k \qquad (2)$$

(where Mo is molybdenum, V is vanadium, W is tungsten, Cu is copper, A is at least an element selected from antimony, niobium and tin, B is at least an element selected from phosphorus, tellurium, lead, arsenic and zinc, and O is oxygen; e, f, g, h, i, j and k denote atomic ratios of Mo, V, W, Cu, A, B and O, respectively; and where e is 12, 2≦f≦15, 0≦g≦10, 0<h≦6 (preferably 0.01≦h≦6), 0≦i≦6, 0≦j≦5, and k is a numerical value determined by the extents of oxidation of the other elements), carried on said modified carrier is provided.

According to the invention, furthermore, a process for preparation of acrylic acid by oxidizing acrolein at vapor phase with molecular oxygen or a molecular oxygen-containing gas in the presence of a catalyst is provided, the process being characterized by the use of said complex oxide catalyst as the catalyst.

[Embodiments of the Invention]

As the inert carrier, any of those generally used for preparation of various catalysts, in particular, catalysts for oxidation of acrolein, can be used, the typical ones being silica, alumina, silica-alumina, silicon carbide, silicon nitride, titanium dioxide, zirconium oxide and the like. Of those alumina and silica-alumina are the preferred.

The modified carrier of the invention is formed by having such an inert carrier carry on at least a part of its surface an oxide represented by the general formula (1). That is, the modified carrier of the invention is formed of an inert carrier and an oxide of the general formula (1) which is carried on at least a part of the surface of the inert carrier. The form of the oxide of the general formula (1) which is carried on the inert carrier is subject to no critical limitation, but it is normally preferred that an effective amount of the oxide covers the inert carrier with an approximately uniform thickness.

The amount of the oxide of the general formula (1) which is to be carried on the inert carrier is such that can at least exhibit sufficient carriage effect. More specifically, it is satisfactory to have the inert carrier carry thereon an oxide of the general formula (1) at a carriage ratio of 1–50%, preferably 3–30%, said ratio being calculated by the following equation:

carriage ratio (%)=[1-(weight of inert carrier/weight of modified carrier)]×100.

Where the carriage ratio is less than 1%, the effect of the modified carrier cannot be sufficiently obtained. Whereas, when it exceeds 50%, the surface properties of the inert carrier itself such as coarseness and porosity are impaired by the supported oxide, to reduce adhesion between the modified carrier and the catalytic component supported thereon, giving rise to such a problem as peel-off of the catalyst component.

The condition of carriage of the oxide of the general formula (1) on the inert carrier surface in the modified carrier of the invention can be confirmed by means of a linear or planar analysis of cross-section with EPMA (Electron Probe Micro Analyzer).

Among the oxides which are expressed by the general formula (1), those whose X-component is magnesium, calcium, strontium or barium; Y-component is silicon or aluminum; Z-component is sodium, potassium, iron, cobalt, nickel or boron; and where a=1, 0<b≦100 (preferably 0.01≦b≦100) and 0≦c≦10, are preferred.

The modified carrier of the invention can be prepared following the generally practiced methods for having an inert catalyst carry the substance to be supported. For example, compounds containing at least an element selected from alkaline earth metals; at least an element selected from silicon, aluminum, zirconium and titanium; and optionally at least an element selected from Group IA elements and Group IIIb elements of the periodic table, boron, iron, bismuth, cobalt, nickel and manganese are carried and deposited on an inert carrier, in such a form of an aqueous solution, suspension or powder by such means as impregnation, spraying or evaporation to dryness, and if necessary dried, and heat-treated at a temperature range of 500° C.–2,000° C., preferably 700° C.–1,800° C., inter alia, 800° C.–1,700° C., for around 1–10 hours. Obviously, it is permissible to use, as one of the starting compounds, a compound concurrently containing X-component and Y-component.

The complex oxide catalyst of the invention is a catalyst formed by carrying on said modified carrier a complex catalyst comprising molybdenum and vanadium, preferably a complex oxide which is expressed by the earlier given general formula (2). Such a complex oxide catalyst can be prepared in the manner generally practiced for preparing this kind of complex oxide catalysts, excepting that the modified carrier is used. For example, it can be prepared by such a method in which the starting compounds are deposited on the modified carrier and thereafter converted to the complex oxide by calcination.

Among the complex oxides which are expressed by the general formula (2), those whose A-component is antimony or tin, B-component is phosphorus, tellurium and zinc; and where e=12, 2≦f≦15, 0≦g≦10, 0≦h≦6 (preferably 0.01≦h≦6), 0≦i≦6 and 0≦j≦5 are preferred.

Shapes of the modified carrier and the complex oxide catalyst of the invention are not critical. Any optional forms such as ring, sphere, column and the like can be selected. The average diameter as the catalyst is 1–15 mm, preferably 3–10 mm.

Suitable amount of the complex oxide containing molybdenum and vanadium to be supported on the modified carrier is 10–70%, preferably 15–50%, in terms of the supported ratio (%) as calculated by the following equation:

supported ratio (%)=[(weight of the complex oxide)/(weight of the modified carrier)+(weight of the complex oxide)]×100

In preparing complex oxide catalyst of the invention, those well known additives having the effect of improving the strength and attrition resistance of catalysts, such as inorganic fibers, e.g., glass fiber or various whiskers may be added. Also for controlling physical properties of the catalyst with good reproducibility, additives such as ammonium nitrate, cellulose, starch, polyvinyl alcohol, stearic acid and the like may be used.

The complex oxide catalyst of the invention is obtained upon calcining the catalyst precursor as deposited on the modified carrier at 300° C.–600° C., preferably at 350° C.–500° C., for about 1–10 hours.

The acrylic acid production process of the invention can be carried out following any of generally practiced methods for producing acrylic acid through vapor phase oxidation of acrolein, except that the above-described complex oxide catalyst is used. Therefore, the apparatus and operating conditions in carrying out the production are not critical. That is, as the reactor, an ordinary fixed bed reactor, fluidable bed reactor or moving bed reactor can be used, and the reaction can be carried out under the conditions conventionally employed for production of acrylic acid from acrolein through vapor phase catalytic oxidation reaction. For example, a gaseous mixture of 1–15 volume % of acrolein, 0.5–25 volume % of oxygen, 1–30 volume % of steam and 20–80 volume % of an inert gas like nitrogen, is contacted with a complex oxide catalyst of the invention at temperatures ranging from 200 to 400° C., under a pressure of 0.1–1 MPa and at a space velocity of 300–5,000 h$^{-1}$ (STP) to produce acrylic acid.

Besides such gaseous mixtures of acrolein, oxygen and inert gas, acrolein-containing gaseous mixtures which are obtained through direct oxidation of propylene may also be used as the starting gas, if necessary after adding air or oxygen and steam. Presence of such side products as acrylic acid, acetic acid, carbon oxide and propane or unreacted propylene in the acrolein-containing gaseous mixtures obtained upon direct oxidation of propylene is in no way detrimental to the complex oxide catalyst used in this invention.

[Effect of the Invention]

According to the invention, high-activity and high-performance catalysts are obtainable with good reproducibility. Moreover, because the complex oxide catalysts of the invention maintain the high activity levels over prolonged periods, acrylic acid can be stably produced at high yields over prolonged periods according to the process of the invention.

EXAMPLES

Hereinafter the invention is explained more specifically referring to working Examples, it being understood that the Examples incur no restricting effect on the invention.

In the Examples, the acrolein conversion, acrylic acid selectivity and acrylic acid yield were calculated according to the following equations:

acrolein conversion (%)=[(mol number of reacted acrolein)/(mol number of fed acrolein)]×100 acrylic acid selectivity (%)=[(mol number of formed acrylic acid)/(mol number of reacted acrolein)]×100 acrylic acid yield (%)=[(mol number of formed acrylic acid)/(mol number of fed acrolein)]×100

Example 1
[Preparation of a Modified Carrier Formed of an Inert Carrier Carrying an Oxide (Mg—Si—Al)]

Into 2,000 ml of pure water, 890 g of magnesium nitrate and 130 g of aluminium nitrate were dissolved under heating and stirring. Into the formed solution, 1563 g of 20 weight % silica sol was added and mixed, followed by addition of 2,000 g of silica-alumina spherical carrier of 5 mm in average particle diameter as an inert carrier. The system was evaporated to dryness under heating. Subsequently the heating temperature was raised stagewisely. Upon calcination at 1,300° C. for 3 hours at the final stage, a modified carrier [modified carrier (1)] was obtained. The composition of the carried oxide (excepting oxygen, like in all of the following compositions) was as follows:

$$Mg_1Si_{1.5}Al_{0.1}.$$

The carriage ratio was 18.3%.
[Preparation of Complex Oxide Catalyst]
Into 2,000 ml of pure water, 350 g of ammonium paramolybdate, 96.6 g of ammonium metavanadate and 44.6 g of ammonium paratungstate were dissolved under heating and stirring. Separately, 87.8 g of cupric nitrate and 4.8 g of antimony trioxide were added to 200 g of pure water under heating and stirring. Thus obtained two liquids were mixed and together poured into a porcelain evaporator on hot water bath. Then, 1,200 ml of the modified carrier (1) was added, followed by evaporation to dryness under stirring to have the catalyst deposited on the modified carrier (1). The carrier-supported catalyst was calcined at 400° C. for 6 hours to provide a complex oxide catalyst [Catalyst (1)]. The composition of metallic elements (excepting oxygen, as in all of hereafter indicated compositions) of this Catalyst (1) was as follows:

$$Mo_{12}V_5W_1Cu_{2.2}Sb_{0.5}.$$

The supported ratio was 22%.
[Oxidation Reaction]
A stainless steel reaction tube of 25 mm in diameter was charged with 1,000 ml of thus obtained Catalyst (1), and into which a gaseous mixture of 5 volume % of acrolein, 5.5 volume % of oxygen, 25 volume % of steam and 64.5 volume % of inert gas comprising nitrogen and the like was introduced. The reaction was carried out at 260° C. and at a space velocity (SV) of 1,500 h$^{-1}$ (STP). The catalyst performance at the initial period and after 8,000 hours' reaction was as shown in Table 1.

Comparative Example 1

Catalyst (2) was prepared in the identical manner with the catalyst preparation in Example 1, except that the inert carrier was used as it was. The oxidation reaction was carried out under identical conditions with those of Example 1, except that the Catalyst (2) was used. The result was as shown in Table 1.

Example 2
[Preparation of a Modified Carrier Formed of an Inert Carrier Carrying an Oxide (Ca—Ba—Si)]
Into 2,000 ml of pure water, 8.2 g of calcium nitrate, 9.1 g of barium nitrate and 1.5 g of sodium nitrate were dissolved under heating and stirring. To this solution 563 g of 20 weight % silica sol was added and mixed, and into the liquid mixture 2,000 g of silica-alumina spherical carrier having an average particle diameter of 5 mm was added as an inert carrier, followed by evaporation to dryness under heating. The heat-treating temperature was raised stagewisely. Upon 5 hours' calcination at 1,400° C. at the final stage, a modified carrier [modified carrier (2)] was obtained. The composition of the carried oxide was as follows:

$$(Ca_{0.5}Ba_{0.5})_1Si_{27}Na_{0.25}.$$

The carriage ratio was 5.4%.
[Preparation of a Complex Oxide Catalyst]
A complex oxide catalyst [Catalyst (3)] was prepared in the identical manner with Example 1, except that the modified carrier (1) was replaced with the modified carrier (2).
[Oxidation Reaction]
The reaction was carried out under identical conditions with those in Example 1, except that Catalyst (1) was replaced with Catalyst (3). The result was as shown in Table 1.

Example 3
[Preparation of a Modified Carrier Formed of an Inert Carrier Carrying an Oxide (Mg—Si—Al)]
Into 2,000 ml of pure water, 1423 g of magnesium nitrate, 112 g of iron nitrate, 5.6 g of potassium nitrate and 208 g of aluminum nitrate were dissolved under heating and stirring. The solution was mixed with 2500 g of 20 weight % silica sol, and into the liquid mixture 2,000 g of silica-alumina spherical carrier having an average particle diameter of 5 mm was added as an inert carrier, followed by evaporation to dryness under heating. Thereafter the heat-treating temperature was raised stagewisely, and upon 3 hours' calcination at 1,200° C. at the final stage, a modified carrier [modified carrier (3)] was obtained. The composition of the carried oxide was as follows:

$$Mg_1Si_{1.5}Al_{0.1}K_{0.01}Fe_{0.05}.$$

The carried ratio was 27%.
[Preparation of Complex Oxide Catalyst]
A complex oxide catalyst [Catalyst (4)] was prepared in the identical manner with the catalyst preparation in Example 1, except that the modified carrier (3) was used in place of the modified carrier (1).
[Oxidation Reaction]
The reaction was carried out under identical conditions with those in Example 1, except that Catalyst (1) was replaced with Catalyst (4). The result was as shown in Table 1.

Example 4
[Preparation of a Modified Carrier Formed of an Inert Carrier Carrying an Oxide (Sr—Si—Al)]
Into 2,000 ml of pure water, 183.6 g of strontium nitrate and 650 g of aluminium nitrate were dissolved under heating and stirring. The solution was mixed with 625 g of 20 weight % silica sol, and into the liquid mixture 2,000 g of a silica-alumina spherical carrier having an average particle diameter of 5 mm was added as an inert carrier, followed by evaporation to dryness under heating. The heat-treating temperature was raised stagewisely, and upon 3 hours' calcination at 1,500° C. at the final stage, a modified carrier [modified carrier (4)] was obtained. The composition of the carried oxide was as follows:

$$Sr_1Si_{2.4}Al_2.$$

The carriage ratio was 12.6%.
[Preparation of a Complex Oxide Catalyst]
A complex oxide catalyst [Catalyst (5)] was prepared in the identical manner with the catalyst preparation in Example 1, except that the modified carrier (4) was used in place of the modified carrier (1).
[Oxidation Reaction]
The reaction was carried out under identical conditions with those in Example 1, except that Catalyst (1) was replaced with Catalyst (5). The result was as shown in Table 1.

Example 5
[Preparation of a Modified Carrier Formed of an Inert Carrier Carrying an Oxide (Mg—Si)]
Into 2,000 ml of pure water, 300 g of magnesium silicate (manufactured by Nakarai Tesque Co.) was added, and further 2,000 g of silica-alumina spherical carrier having an average particle diameter of 5 mm was added as an inert carrier, followed by evaporation to dryness under heating. Thereafter the heat-treating temperature was raised stagewisely, and upon 2 hours' calcination at 1,700° C. at the final stage, a modified carrier [modified carrier (5)] was obtained. The composition of the carried oxide was as follows:

$$Mg_1Si_{1.5}.$$

The carriage ratio was 9.7%.
[Preparation of a Complex Oxide Catalyst]
A complex oxide catalyst [Catalyst (6)] was prepared in the identical manner with the catalyst preparation of Example 1, except that the modified carrier (5) was used in place of the modified carrier (1).
[Oxidation Reaction]
The reaction was carried out under identical conditions with those in Example 1, except that Catalyst (1) was replaced with Catalyst (6). The result was as shown in Table 1.

TABLE 1

| Catalyst No. | | | Reaction Temp. (° C.) | Acrolein conversion (%) | Acrylic Acid Selectivity (%) | Acrylic Acid Yield (%) |
|---|---|---|---|---|---|---|
| Example 1 | (1) | Initial stage of reaction | 260 | 99.2 | 96.0 | 95.2 |
| | | After 8,000 hrs. | 270 | 99.2 | 95.8 | 95.0 |
| Comparative Example 1 | (2) | Initial stage of reaction | 260 | 98.4 | 94.4 | 92.9 |
| | | After 8,000 hrs. | 287 | 98.6 | 93.9 | 92.6 |
| Example 2 | (3) | Initial stage of reaction | 260 | 99.0 | 95.4 | 94.4 |
| | | After 8,000 hrs. | 271 | 99.0 | 95.3 | 94.3 |
| Example 3 | (4) | Initial stage of reaction | 260 | 99.3 | 95.9 | 95.2 |
| | | After 8,000 hrs. | 269 | 99.2 | 95.7 | 94.9 |
| Example 4 | (5) | Initial stage of reaction | 260 | 99.1 | 95.6 | 94.7 |
| | | After 8,000 hrs. | 270 | 99.0 | 95.5 | 94.5 |
| Example 5 | (6) | Initial stage of reaction | 260 | 99.0 | 95.1 | 94.1 |
| | | After 8,000 hrs. | 273 | 99.1 | 95.0 | 94.1 |

What is claimed is:

1. A complex oxide catalyst in which a complex oxide containing molybdenum and vanadium is supported on a carrier, characterized in that said complex oxide containing molybdenum and vanadium is a complex oxide which is expressed by the following general fomula (2):

$$Mo_e V_f W_g Cu_h A_i B_j O_k \qquad (2)$$

(where MO is molybdenum, V is vanadium, W is tungsten, Cu is copper, A is selected from the group consisting of antimony, niobium and tin; B is selected from the group consisting of phosphorus, tellurium, lead, arsenic and zinc, and O is oxygen; e, f, g, h, i, j and k denote atomic rations of Mo, V, W, Cu, A, B and O, where a=12, $2 \leq f \leq 15$, $0 \leq g \leq 10$, $0 \leq h \leq 6$, $0 i \leq 6$, $0 \leq j \leq 5$, and k is a numerical value determined by the valences and number of occurrences of the other elements), and said carrier is a modified carrier having on a surface of an inert carrier an oxide expressed by the formula (1):

$$X_a Y_b Z_c O_d \qquad (1)$$

(wherein X is selected from the group consisting of alkaline earth metals; Y is selected from the group consisting of silicon, aluminum, titanium and zirconium; Z is selected from the group consisting of Group IA elements and Group IIB elements of the periodic table, boron, iron, bismuth, cobalt, nickel and manganese; of X, Y, Z and O, respectively, and where a=1, 0<b<100 and 0<c<10 and d is a numerical value determined by the valances and number of occurrences of the other elements).

2. The complex oxide catalyst as described in claim 1, in which said inert carrier is selected from the group consisting of silica, alumina, silica-alumina, silicon carbide, silicon nitride, titanium dioxide and zirconium oxide.

* * * * *